(12) United States Patent  (10) Patent No.: US 6,171,249 B1
Chin et al.  (45) Date of Patent: Jan. 9, 2001

(54) ULTRASOUND GUIDED THERAPEUTIC AND DIAGNOSTIC DEVICE

(75) Inventors: Milton Chin, Trumbull; Gregory S. Konstorum, Stamford, both of CT (US)

(73) Assignee: Circon Corporation, Goleta, CA (US)

( * ) Notice: Under 35 U.S.C. 154(b), the term of this patent shall be extended for 0 days.

(21) Appl. No.: 09/170,023

(22) Filed: Oct. 13, 1998

Related U.S. Application Data

(60) Provisional application No. 60/061,835, filed on Oct. 14, 1997.

(51) Int. Cl.[7] ........................................... A61B 8/00
(52) U.S. Cl. ............................ 600/461; 604/272; 600/143
(58) Field of Search ..................... 600/437, 459, 600/461, 462–463, 466–467, 471, 104, 143; 606/185; 604/272

(56) References Cited

U.S. PATENT DOCUMENTS

| | | | |
|---|---|---|---|
| 4,346,717 | * | 8/1982 | Haerten .................. 600/461 |
| 4,763,662 | * | 8/1988 | Yokoi ..................... 600/461 |
| 5,158,086 | * | 10/1992 | Brown et al. ............ 600/459 |
| 5,398,690 | * | 3/1995 | Batten et al. ............ 600/461 |
| 5,437,283 | * | 8/1995 | Ranalletta et al. ....... 600/459 |
| 5,601,588 | * | 2/1997 | Tonomura et al. ....... 606/185 |
| 5,634,466 | * | 6/1997 | Gruner .................... 600/459 |
| 5,873,828 | * | 2/1999 | Fujio et al. ............. 600/461 X |

* cited by examiner

Primary Examiner—Francis J. Jaworski
(74) Attorney, Agent, or Firm—Perman & Green, LLP

(57) ABSTRACT

A medical instrument having a shaft with a bending neck, an ultrasound device at a distal end of the bending neck, a working channel extending through the shaft with a tubular working channel made from superelastic material extending to an opening proximate the ultrasound device, and a biopsy needle located in the working channel. The needle is comprised of superelastic material and is extendible and retractable out the working channel opening in an imaging path of the ultrasound device.

9 Claims, 6 Drawing Sheets

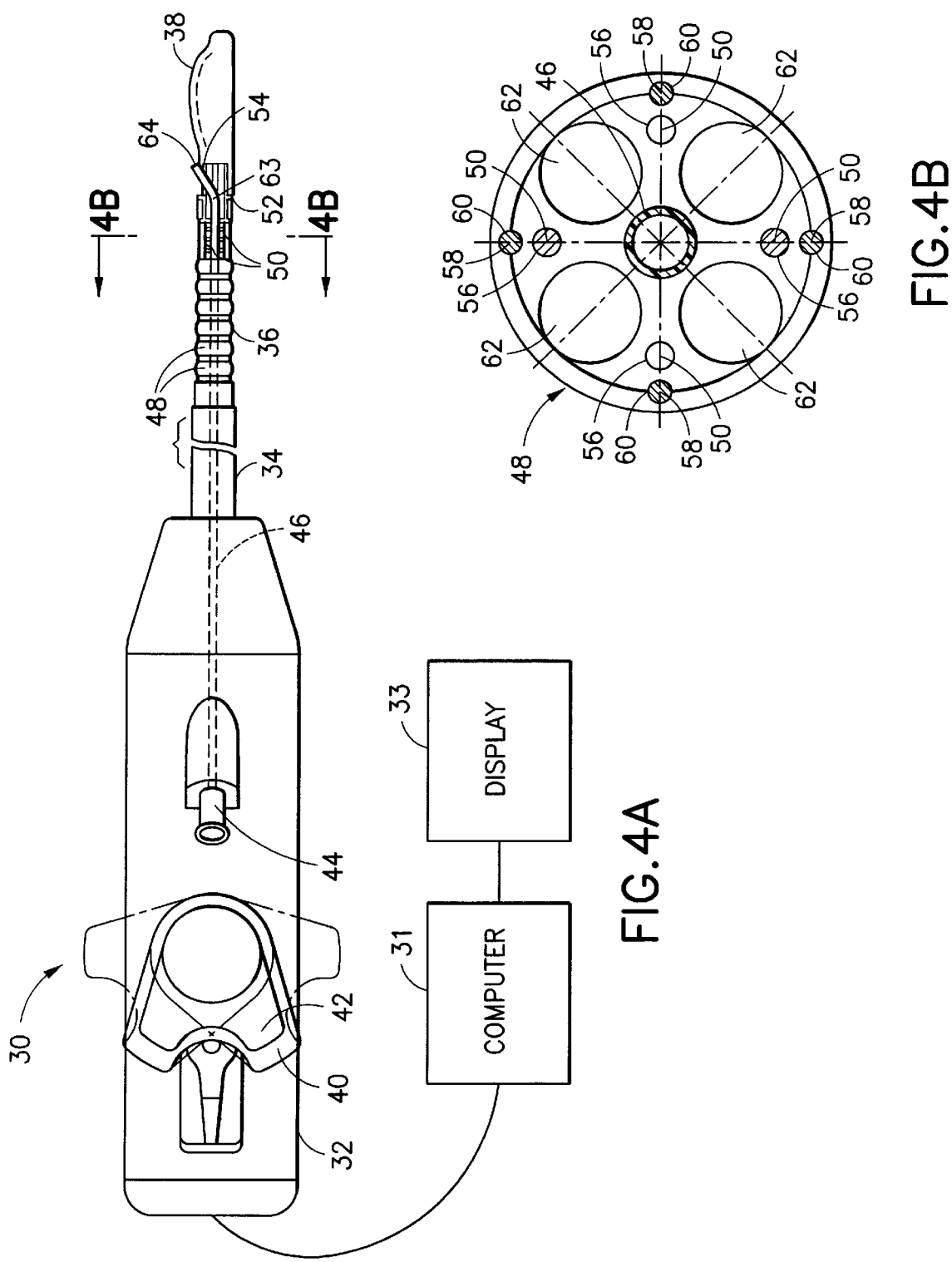

ULTRASOUND GUIDED THERAPEUTIC AND DIAGNOSTIC DEVICE

CROSS-REFERENCE TO RELATED APPLICATION

This application claims the benefit of U.S. provisional application Ser. No. 60/061,835 filed Oct. 14, 1997.

BACKGROUND OF THE INVENTION

1. Field of the Invention

The present invention relates to a medical device and, more specifically, to an ultrasound device.

2. Prior Art

With the advent of laparoscopic surgery, ultrasound imaging can be used to image beneath the surface of organs. Implementation is achieved by the introduction of an ultrasound imaging probe through a cannula. FIG. 1A shows the end of one such probe 10 with a distal transducer array 12 on the end of its shaft 14. The array 12 is positioned at tissue 16 to be imaged. Images are generated by the transducer array located at the end of a shaft, and are transmitted via a signal cable through the shaft and handle. Images are reconstructed by computer connect by cable to the probe handle and displayed on a CRT screen. A typical ultrasound image 15 corresponding to FIG. 1A is shown in FIG. 1B. It is desirable to have a flexible tip to the shaft such that the transducer array can be bent relative to the axis of the shaft. A skilled surgeon can maneuver the probe tip to the organ/area of interest.

In conjunction with ultrasound imaging, there is also a need to obtain biopsy samples of suspicious areas. The use of ultrasound allows the surgeon to guide the biopsy procedure. This procedure, generically called ultrasound guided biopsy is depicted in FIG. 2A. The surgeon positions the probe 10 and, using the ultrasound image 15 shown in FIG. 2B that is viewed on a display, guides the biopsy needle 18 to the suspect area B. The advantage of this method is the accuracy by which a laparoscopic surgeon can obtain biopsy samples.

In laparoscopic surgery, as illustrated in FIG. 2A, both probes and needle are introduced via separate cannulas. The workload on the surgeon to execute a biopsy is high as he must coordinate the location of two objects (probe and needle) while looking at a real time ultrasound image and a video image. U.S. Pat. No. 5,437,283 describes a laparascopic ultrasound probe with integrated biopsy capabilities. The probe can function as an image only probe and, with an attachment, as a biopsy probe. FIG. 3A schematically shows the ultrasound probe 20 and biopsy device 22 of U.S. Pat. No. 5,437,283. The biopsy device 22 generally comprises a needle 24, a guide 25 and a gun 27. By virtue of the attachment, the biopsy needle 24, made of conventional stainless steel, is constrained to follow a sampling trajectory that always passes within of the ultrasound image (See FIG. 3C). This approach greatly reduces the workload of the physician performing laparoscopic ultrasound guided biopsy.

The use of laparoscopic ultrasound probes with deflectable tips exposes the shortcomings of U.S. Pat. No. 5,437,283. Probes with the attachment 22 will need a larger cannula in the patient. The biopsy needle 24 is constrained to be parallel with the rigid shaft 26. Deflectable tips 28 can only be two-way deflectable (not four-way deflectable) because deflection on the perpendicular lateral direction from that illustrated in FIG. 2A will cause the image to be out of the trajectory plane of the biopsy needle. It is obvious that the bending neck 30 can only deflect in one direction, away from the path of the needle 24, otherwise the tip 28 would block the path of the needle. Because the tip 28 can only be deflected away from the path of the needle 24 in one direction, this limits the flexibility of the probe. Another problem is that, at the extremes of deflection, the image of the trajectory is small. Furthermore, it is not possible to preprogram the trajectory of the needle's path because the angle which the biopsy needle enters the ultrasound image will be a function of the deflection angle of the neck 30 and tip 28. Thus the target line for the biopsy needle cannot be determined in advance. It can only be estimated from the deflection angle.

SUMMARY OF THE INVENTION

In accordance with one embodiment of the present invention an endoscope is provided comprising a shaft, an ultrasound device, a working channel, and a biopsy needle. The shaft has a bending neck. The ultrasound device is located at a distal end of the bending neck. The working channel extends through the shaft and bending neck and has an opening proximate the ultrasound device. The biopsy needle is located in the working channel. The needle is comprised of superelastic material and is extendible and retractable out the working channel opening proximate the ultrasound device.

In accordance with another embodiment of the present invention a medical needle assembly is provided having a front end with an aperture. The needle assembly has a first member forming the front end which is comprised of a shape memory alloy with superelastic properties allowing the first member to resiliently deform with a strain of at least 6 percent.

In accordance with another embodiment of the present invention a medical system is provided having an ultrasound probe, a display, and means for displaying a combined image on the display. The ultrasound probe has means for extending a needle from the probe. The display is connected to the probe. The means for displaying a combined image on the display can display an ultrasound image from the probe and a computer generated image of an expected path of the needle relative to the ultrasound image if the needle were to be extended from the probe.

BRIEF DESCRIPTION OF THE DRAWINGS

The foregoing aspects and other features of the present invention are explained in the following description, taken in connection with the accompanying drawings, wherein:

FIG. 4A is a side view of a device incorporating features of the present invention with a distal end shaft covering removed;

FIG. 4B is a cross-sectional view taken along line 4B—4B of FIG. 4A;

DETAILED DESCRIPTION OF THE PREFERRED EMBODIMENT

Figure 1A:
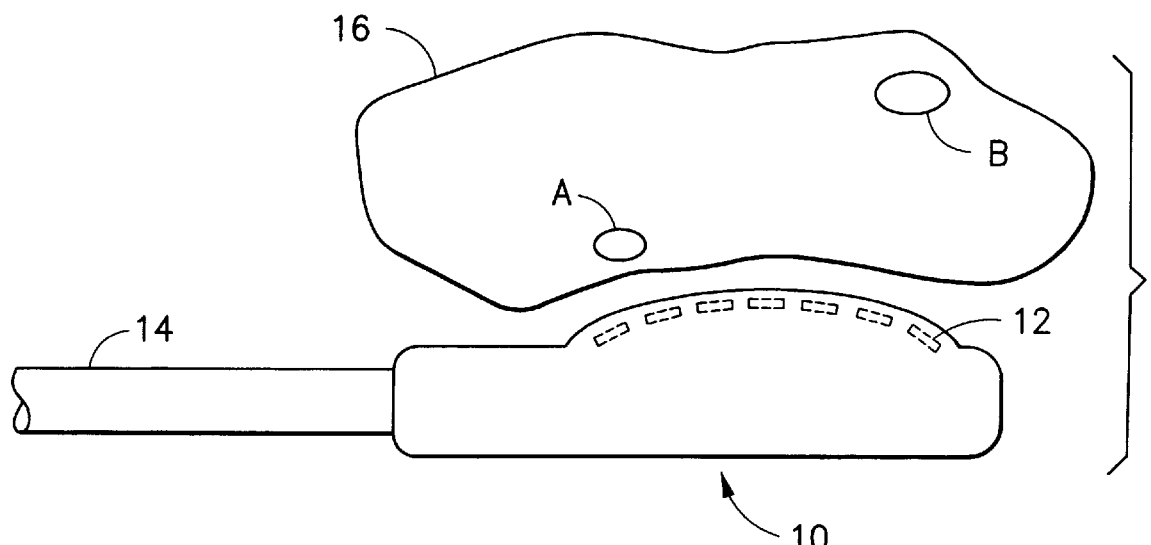
FIG. 1A is a schematic view of a distal end of a laparoscopic ultrasound probe known in the prior art in position relative to body tissue to be imaged.
Figure 1B:
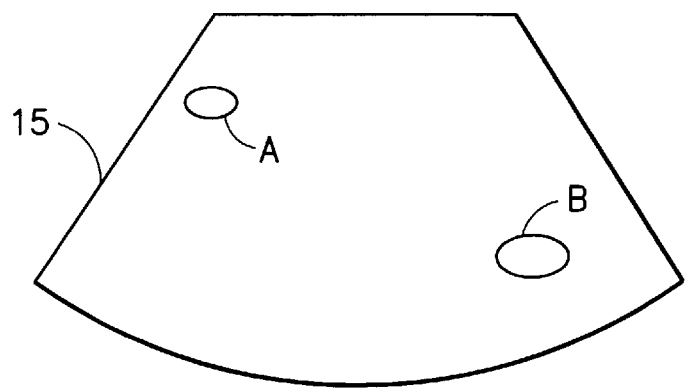
FIG. 1B is a schematic view of an ultrasound image generated from FIG. 1A.
Figure 2A:
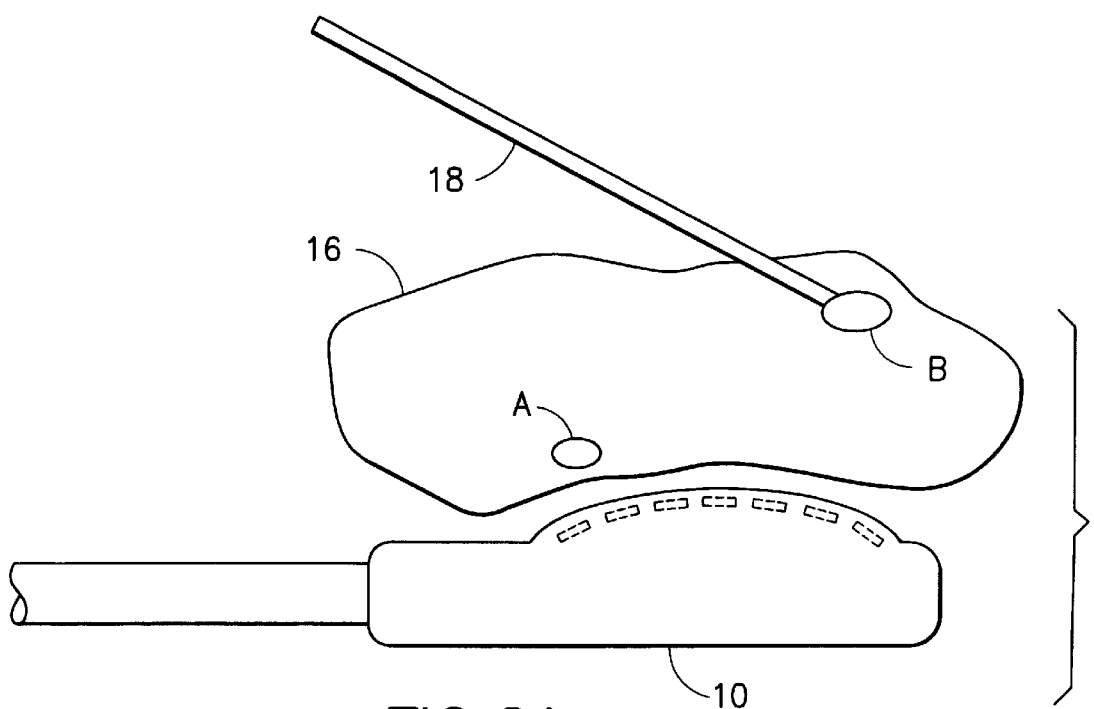
FIG. 2A is a schematic view as in FIG. 1A showing insertion of a biopsy needle to a suspect area through a separate cannula.
Figure 2B:
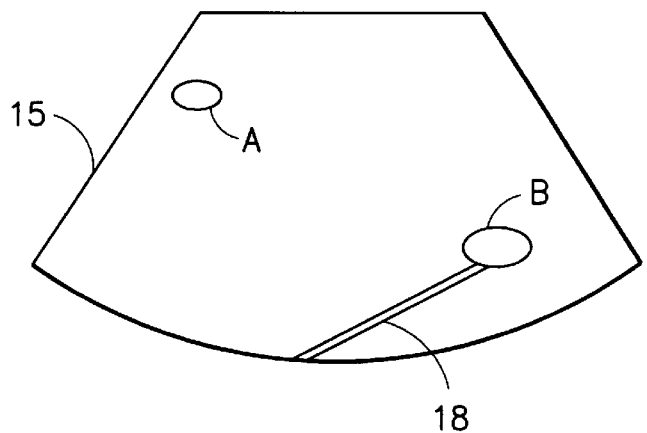
FIG. 2B is a schematic view of an ultrasound image generated from FIG. 2A.
Figure 3A:
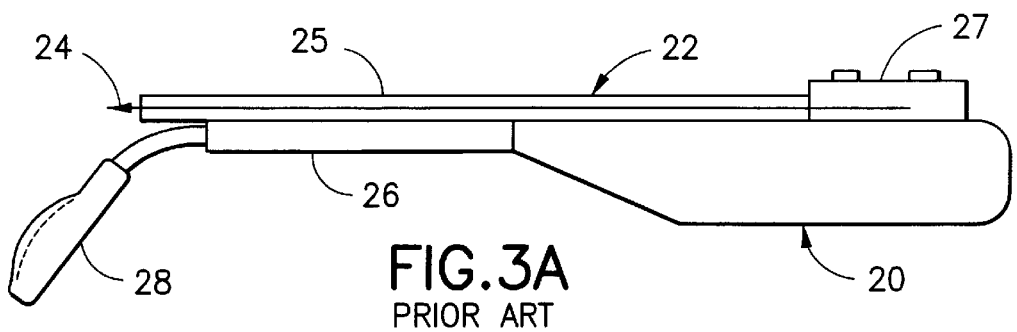
FIG. 3A is a schematic side view of a prior art laparoscopic ultrasound probe with an integrated biopsy actuator.
Figure 3B:
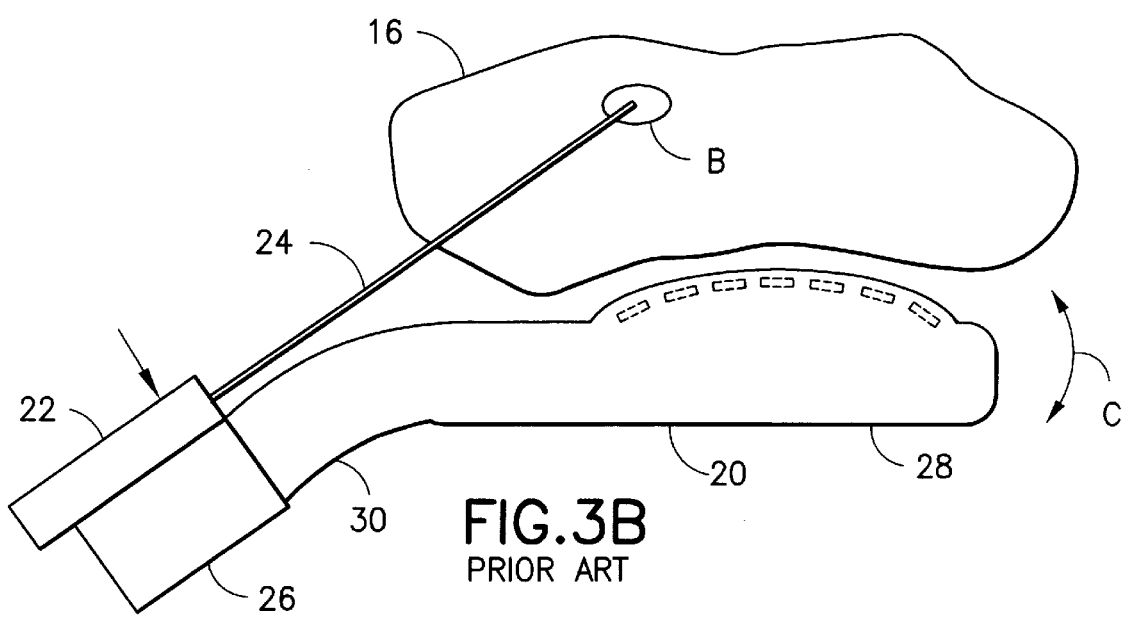
FIG. 3B is an enlarged schematic view of the distal end of the device shown in FIG. 3A located at tissue in a patient's body and showing the biopsy needle extended to tissue to be biopsied.
Figure 3C:
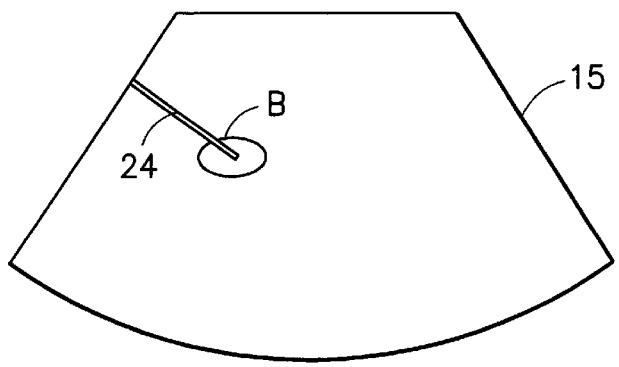
FIG. 3C is a schematic view of an ultrasound image generated from FIG. 3B.

Referring to FIG. 4A, a laparoscopic ultrasound probe 30 incorporating features of the present invention is shown. The probe 30 includes a handle section 32, a rigid shaft section 34, a deflectable or bendable neck 36, and a distal end ultrasound section 38. The neck 36 is shown without its flexible cover for the sake of clarity. The handle section 32 has two deflection control knobs 40, 42 that can be moved as illustrated by the dashed lines to provide four-way deflection of the neck 36 by control cables as is well known in the art. Also as is known in the art, the handle section 34 has a connector (not shown) for operably connecting the probe to a computer 31 and image display device 33. The handle section 34 further comprises an inlet port 44. A tube 46, which forms a working channel for the probe, extends from the inlet port 44 to the distal end of the neck 36 proximate the ultrasound section 38. In alternate embodiments other types of handle sections could be provided. The probe could also be merely a two-way deflectable probe.

The rigid shaft section 34 connects the bendable neck section 36 to the handle section 32. Referring also to FIG. 4B, the neck 36 is comprised of rigid disks 48 connected in series by resiliently deflectable alternating pair of pins 50. However, in alternate embodiments, any suitable type of controllably deflectable or bendable neck could be provided. The tube 46 passes through a center channel in the disks 48 and curves laterally outward at the distal end of the neck 36. In a preferred embodiment the tube 46 is comprised of a shape memory alloy or superelastic alloy such as Nitinol or Tinel. However, any suitable type of superelastic alloy could be used. As used herein the terms "superelastic material" and "superelastic alloy" are intended to mean shape memory alloys which are being used for their superelastic properties. The distal end member 52 of the neck 36 functions as a structural mount which the ultrasound section 38 is fixedly attached to. The neck distal end member 52 has a hole 54 in one lateral side that the distal end of the tube 46 passes through. FIG. 4B shows one of the disks 48. The disks 48 of the neck also have holes 56 that the pins 50 are mounted in, holes 58 that deflection control cables 60 pass through, and holes 62 that conductors (not shown) to and from the ultrasound section 38 pass through. The distal tip 64 of the tube 46 has an opening that projects towards the imaging path of the ultrasound section 38. In a preferred embodiment the distal tip 64 of the tube is angled at an angle of about 30° relative to the ultrasound section. However, any suitable angle could be provided. The distal tip 64 and the ultrasound section 38 are both fixed relative to the neck end member 52. Thus, they are fixed relative to each other.

Figure 4C:
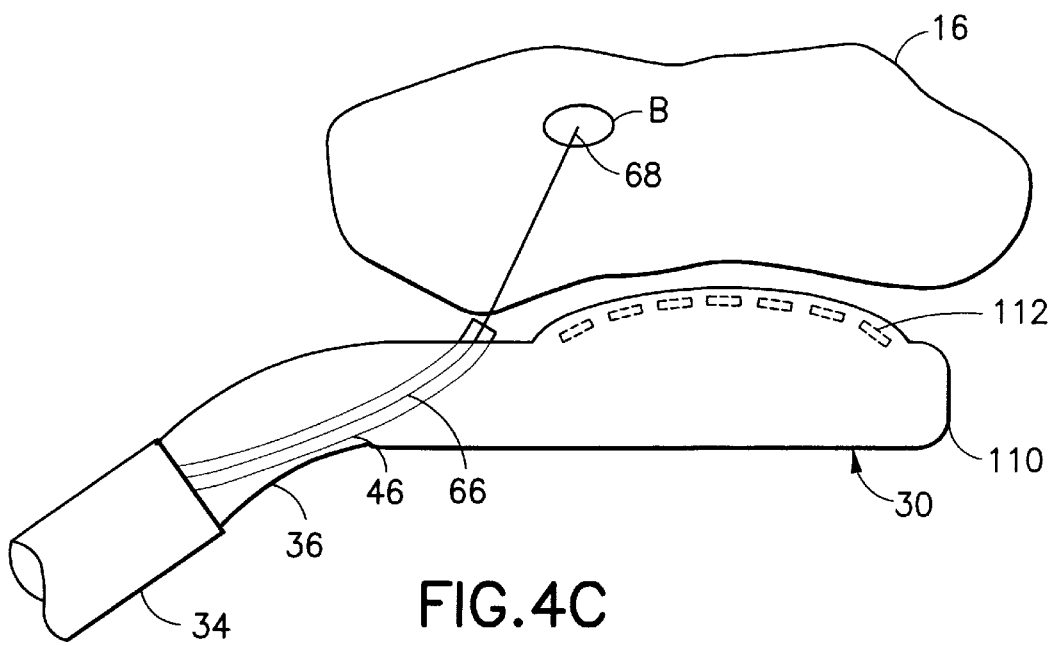
FIG. 4C is an enlarged schematic view of the distal end of the device shown in FIG. 4A in use in a patient to take a biopsy.
Figure 4D:
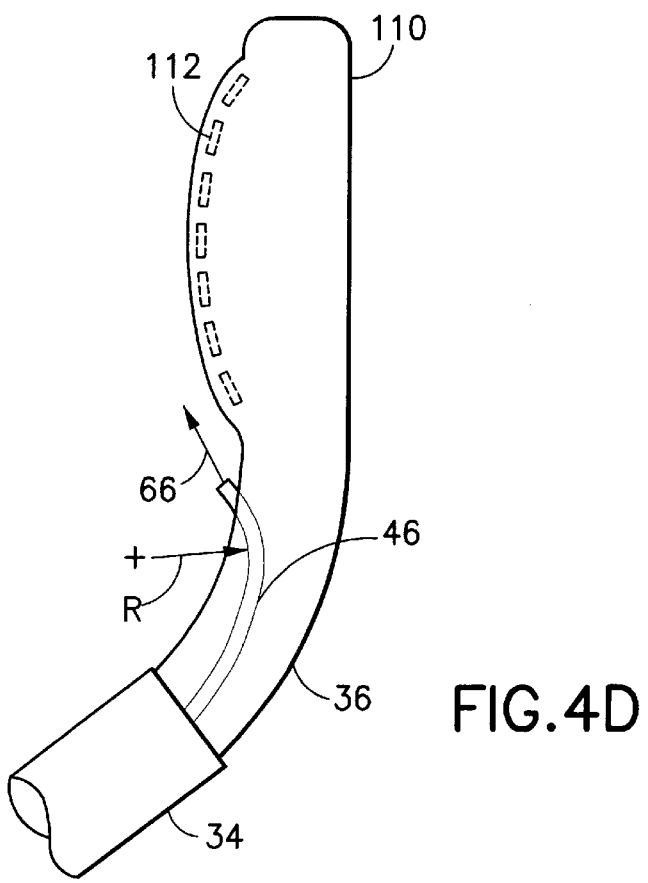
FIG. 4D is an enlarged schematic view of the distal end of the device shown in FIG. 4C with the neck bent in an opposite direction.
Figure 4E:
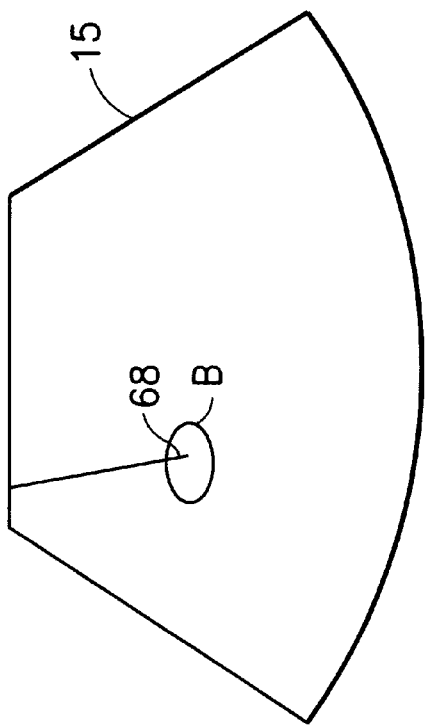
FIG. 4E is a schematic view of an ultrasound image generated from FIG. 4C.
Figure 4F:
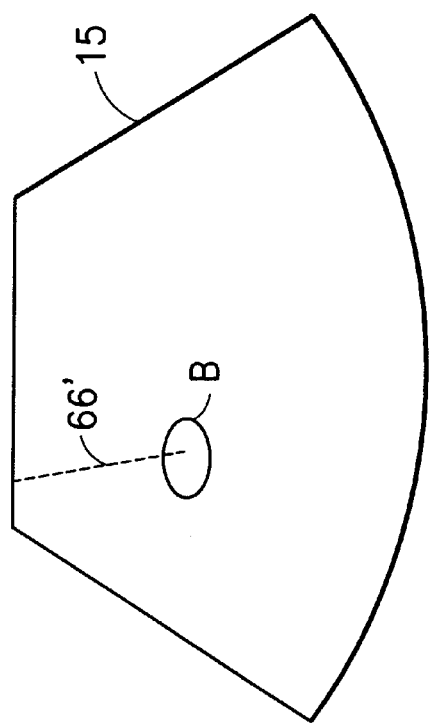
FIG. 4F is a schematic view of an ultrasound image and a computer generated image of predicted needle trajectory if a biopsy needle is extended from the probe.

Referring also to FIG. 4C the present invention is shown with the distal end of probe 30 positioned at the tissue area 16. The surgeon, upon finding the tissue to be biopsied B, will insert the biopsy needle 66 through the inlet port 44 and into the tube 46 (if not already done so) and extend the distal end 68 of the needle 66 into the target area. The needle 66 passes through the working channel formed by the tube 46 and exits next to the transducer array 112. More specifically, the path of the needle 66 will always extend into an image path of the transducer array 112. In addition, as illustrated by FIG. 4D, the ultrasound section 110 having the transducer array 112 can be deflected in an inward direction on a side where the tube 46 has its distal end aperture. Thus, the tube 46 does not block movement of the ultrasound section 110 to one direction as in the prior art. The needle 66, when extended, will also always have the same path in the display image 15 regardless of the direction or degree of bend of the neck 36. FIG. 4E illustrates the ultrasound image 15 that is generated on the display 33 for the arrangement depicted in FIG. 4C. The ultrasound image is basically a thin slice image. The trajectory of the needle caused by the trajectory shape of the distal tip 64 always forces the needle to be within the thin slice image when the needle is extended. Because the path of the needle relative to the ultrasound image will always be the same, the computer 31 can be preprogrammed to generate an image 66' as illustrated in FIG. 4F before the needle 66 is extended. More specifically, the surgeon would preposition the ultrasound section 110 relative to the target area B using the ultrasound image and the computer generated image 66' before extending the needle 66 from the tube 46. Only after the computer generated image 66' is aligned onto the target area B would the surgeon then extend the needle. There is no need for a larger cannula. Full four way deflection is possible with this concept. Regardless of the deflection angle, the biopsy trajectory will always pass through the image field at the same place. This can be pre-programmed into the ultrasound software to generate a predictive phantom image of the expected path of the needle on the display. Thus, the surgeon will know the path before the needle is extended and can position the probe precisely with the use of the phantom image before the needle is extended. Biopsy accuracy is improved and physician workload is reduced.

Figure 5:
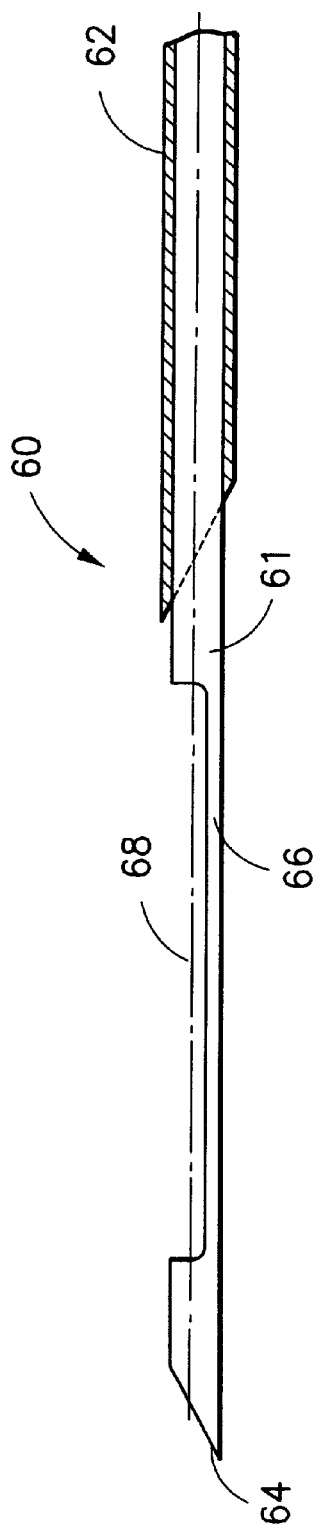
FIG. 5 is an elevational side view with a cut-away section of a front end of a biopsy needle incorporating features of the present invention.

A problem was encountered with the probe 30 described above in relation to use of conventional biopsy needles which are made of steel. In particular, the bendable neck section 36 and the laterally outward bend in the distal end of the tube 46 can form a tight bend as seen by radius R in FIG. 4D. For a typical 10 mm diameter shaft, the bend radius is nominally 1.0 inch. The problem encountered is that conventional steel needles will permanently deform under such curvature and would be no longer useful. Stainless steel needles could be made to bend by making the diameter very small. However, by making the diameter this small, the tissue sample retrieved by the biopsy needle would not be histologically sufficient. In order to overcome this problem the biopsy needle 66 has been manufactured from a shape memory alloy, also known as a superelastic metal alloy. In doing so, such biopsy needles can be bent around a tight radius and still function as a biopsy needle. Superelastic metal alloy needles allow an 18 gauge needle to be used in a 10 mm laparoscope. Referring also to FIG. 5, the front end of a biopsy needle assembly 60 incorporating features of the present invention is shown. The needle assembly 60 has two pieces; an inner shaft 61 and an outer tube 62. The outer tube 62 is shown in cross-section. The outer tube 62 is slidable on the inner shaft 61 between a retracted position as shown in FIG. 5 to a trough closure position. The distal end of the inner shaft 61 has a front barb 64 for piercing through the tissue followed by a lateral trough section 66. The trough section 66 has an aperture or trough 68 extending into the lateral side of the inner shaft 61. With the front end of the needle assembly 60 at the target area and the outer tube 62 in its retracted position, tissue extends into the trough 68. The outer tube 62 can then be extended to cut off tissue in the trough section 66. The needle assembly 60 is then withdrawn with the tissue in the trough 68. The needle needs to be sufficiently rigid to pierce into the tissue without buckling and with path predictability, but also needs to be resiliently bendable in the front curved portion 63 of the working channel tube 46. The high strain capability of the wire 61 and tube 62 of the needle 60 of the present invention, being made of superelastic material, allows the needle 60 to survive a tight bend without buckling and, thus, allows the biopsy needle to still function properly. If one were to use a steel needle in a device bent to a radius of 1.0 inch, the needle would buckle and not function properly. Such a steel needle would exit hole 64 still bent and not properly function as a biopsy needle. In an alternate embodiment, a combined multi-piece steel and superelastic needle could be provided or other combinations of materials could be used.

For the biopsy needle to follow the deflection of the array (up to 90° in all directions) it must survive a tight bend radius. Conventional steel biopsy needles will yield and deform if they were used in such a manner. A biopsy needle manufactured from superelastic metal alloy can be strained to 6–8% and can recover from bends of 1.0 in. radius.

Any deflection of the transducer array will not change the spatial orientation of the needle path relative to the ultrasound section's image path. A biopsy needle that exits this working channel will appear on the ultrasound image at a fixed angle.

The present invention is not limited to superelastic alloys nor only to biopsy needles. Other flexible materials can be used to create therapeutic, such as cryo surgery, as well as diagnosis devices. The present invention can be used in non-laparoscopic procedures.

There are also therapeutic uses other than cryo, such as chemotherapy, which the present invention could be used with. There are also other superelastic materials that can strain up to 18%, but are not yet available in tubular format required for the tube section of the needle. Future products made from these other materials may make even tighter bends possible.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A medical instrument comprising:
   a shaft with a longitudinal bending neck;
   an ultrasound device at a distal end of the bending neck;
   a working channel extending through the shaft and the bending neck and having an opening proximate the ultrasound device, the opening being at a lateral side of the bending neck at a fixed location relative to the ultrasound device; and
   a biopsy needle located in the working channel, the needle being comprised of superelastic material and being extendible and retractable out the working channel opening proximate the ultrasound device,
   wherein a biopsy needle extension path out of the opening from the working channel extends at a fixed angle across an ultrasound path of the ultrasound device, and wherein the working channel is curved along a bendable longitudinal length of the bending neck relative to a longitudinal centerline of the bending neck.

2. A medical instrument as in claim 1 wherein the working channel is a tube comprised of a shape memory alloy.

3. A medical instrument as in claim 1 wherein the working channel is curved proximate the opening.

4. A medical instrument as in claim 3 wherein the working channel extends from the bending neck proximate the opening at an angle of about 30°.

5. A medical instrument as in claim 1 wherein the bending neck comprises rigid disks, resiliently deflectable alternating pairs of pins connecting the disks in series, and deflectable control cables.

6. A medical instrument as in claim 1 wherein the biopsy needle has a first member with a lateral side recess and a second member having a general tube shape slidably mounted on the first member.

7. A medical instrument as in claim 6 wherein both the first and second members are comprised of superelastic material.

8. In a medical needle assembly having a front end with an aperture, wherein the improvement comprises:
   the needle assembly having a first member forming the front end which is comprised of a shape memory alloy with superelastic properties allowing the first member to resiliently deform with a strain of at least 6 percent, and a second member having a general tube shape slidably mounted on the first member, and wherein the second member is comprised of a shape memory alloy with superelastic properties allowing the second member to resiliently deform with a strain of at least 6 percent, and wherein the first member has the aperture in a lateral side thereof.

9. An endoscope comprising:
   a shaft; and
   a working channel extending through the shaft, the working channel comprising a tube of superelastic material and having an opening out of the shaft,
   wherein the shaft comprises a longitudinally bendable section for bending the shaft along a longitudinal centerline of the shaft, wherein a longitudinal centerline of the working channel is curved relative to the longitudinal centerline of the shaft along at least a portion of the bendable section.

* * * * *